US00PP29556P2

(12) United States Plant Patent

Jan Kraan

(10) Patent No.: US PP29,556 P2
(45) Date of Patent: Jul. 31, 2018

(54) *NEPETA* PLANT NAMED 'BOKRATUNE'

(50) Latin Name: *Nepeta kubanica*
Varietal Denomination: Bokratune

(71) Applicant: Kees Jan Kraan, Alphen aan den Rijn (NL)

(72) Inventor: Kees Jan Kraan, Alphen aan den Rijn (NL)

(73) Assignee: BOOT & CO BOOMKWEKERIJEN B.V., Boskoop (NL)

( * ) Notice: Subject to any disclaimer, the term of this patent is extended or adjusted under 35 U.S.C. 154(b) by 0 days.

(21) Appl. No.: 15/530,568

(22) Filed: Jan. 30, 2017

(51) Int. Cl.
*A01H 5/02* (2018.01)

(52) U.S. Cl.
USPC ..... Plt./263.1

(58) Field of Classification Search
USPC ..... Plt./263.1
CPC ..... A01H 5/02; A01H 5/00
See application file for complete search history.

*Primary Examiner* — June Hwu
(74) *Attorney, Agent, or Firm* — Penny J. Aguirre

(57) ABSTRACT

A new cultivar of *Nepeta* named 'Bokratune' that is characterized by its very compact plant habit with a plant height of about 35 cm, its flowers that are deep violet-blue in color, its flowers that are large in size relative to the overall plant size, and its good re-blooming response after dead-heading with new flowers produced in about 4 weeks.

2 Drawing Sheets

Botanical classification: *Nepeta kubanica.*
Variety denomination: 'Bokratune'.

BACKGROUND OF THE INVENTION

The present invention relates to a new and distinct cultivar of *Nepeta kubanica* and will be referred to hereafter by its cultivar name, 'Bokratune'. 'Bokratune' is an herbaceous perennial grown for landscape use.

'Bokratune' arose as part of an ongoing breeding program conducted by the Inventor in Boskoop, The Netherlands with the goal of developing new cultivars of *Nepeta* with unique characteristics. 'Bokratune' derived from open pollination of an unnamed and unpatented proprietary seedling of *Nepeta kubanica* in summer of 2013. The new cultivar was selected from amongst the resulting seedlings as a single unique plant in summer of 2015.

Asexual propagation of the new cultivar was first accomplished by the Inventor by stem cuttings in 2015 in Boskoop, The Netherlands. Asexual propagation of the new cultivar by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Bokratune' as a unique cultivar of *Nepeta.*

1. 'Bokratune' exhibits a very compact plant habit and reaches a height of about 35 cm.
2. 'Bokratune' exhibits flowers that are deep violet-blue in color.
3. 'Bokratune' exhibits flowers that are large in size relative to the overall plant size.
4. 'Bokratune' exhibits a good re-blooming response after dead-heading with new flowers produced in about 4 weeks.

The female parent of 'Bokratune', differs from 'Bokratune' in having a much taller plant size (100 cm in height) and leaves that are much larger in size. 'Bokratune' can be compared to the cultivars *Nepeta subsessilis* 'Cool Cat' (not patented) and *Nepeta* 'Blue Beauty' (not patented). 'Cool Cat' is similar to 'Bokratune' in having a similar plant shape. 'Cool Cat' differs from 'Bokratune' in having a taller plant height (60 cm), a greater plant width, longer and weaker stems, and flowers that are lilac-blue in color. 'Blue Beauty' is similar to 'Bokratune' in having a compact plant habit. 'Blue Beauty' differs from 'Bokratune' in having a taller plant height (45 cm), in producing root suckers (non existing on the new cultivar) and flowers that have a lower lip that is less pronounced.

BRIEF DESCRIPTION OF THE DRAWINGS

The accompanying colored photographs illustrate the overall appearance and distinct characteristics of a 12 month-old plant of the new *Nepeta* as grown in a 17-cm container in Boskoop, The Netherlands.

The photograph in FIG. 1 provides a side view of 'Bokratune' in bloom.

Figure 1:
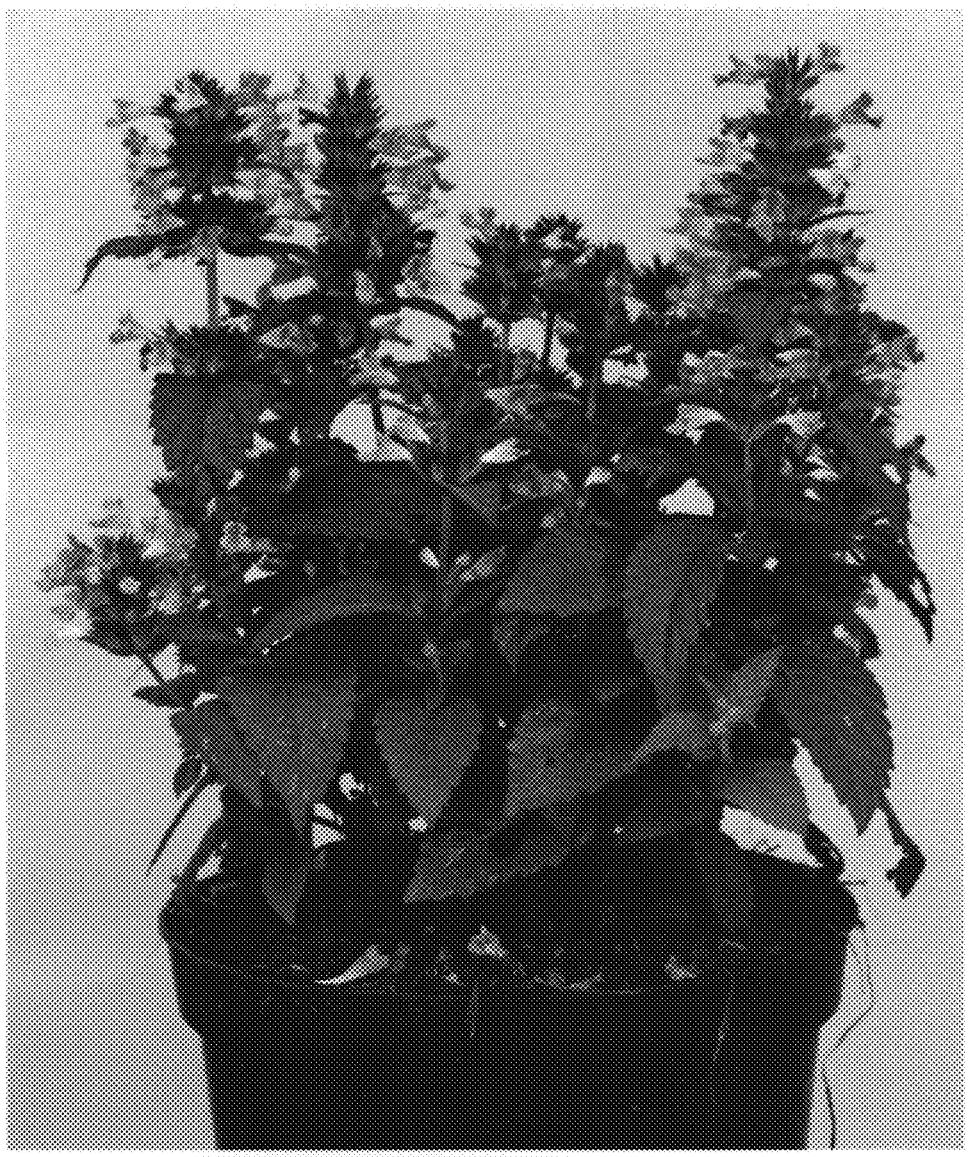
Figure 2:
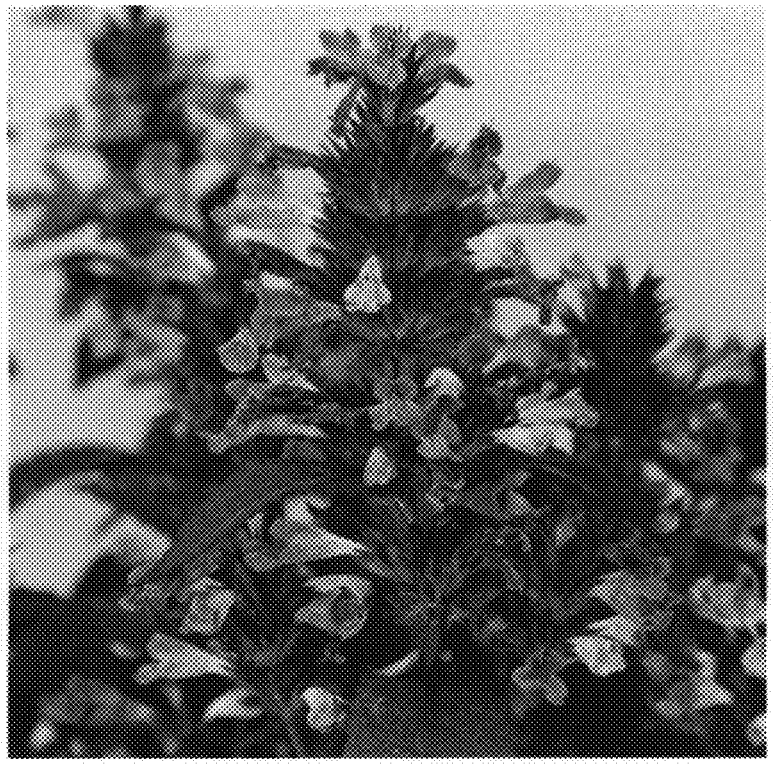

The photograph in FIG. 2 provides a close-up view of an inflorescence of 'Bokratune'.

Figure 3:
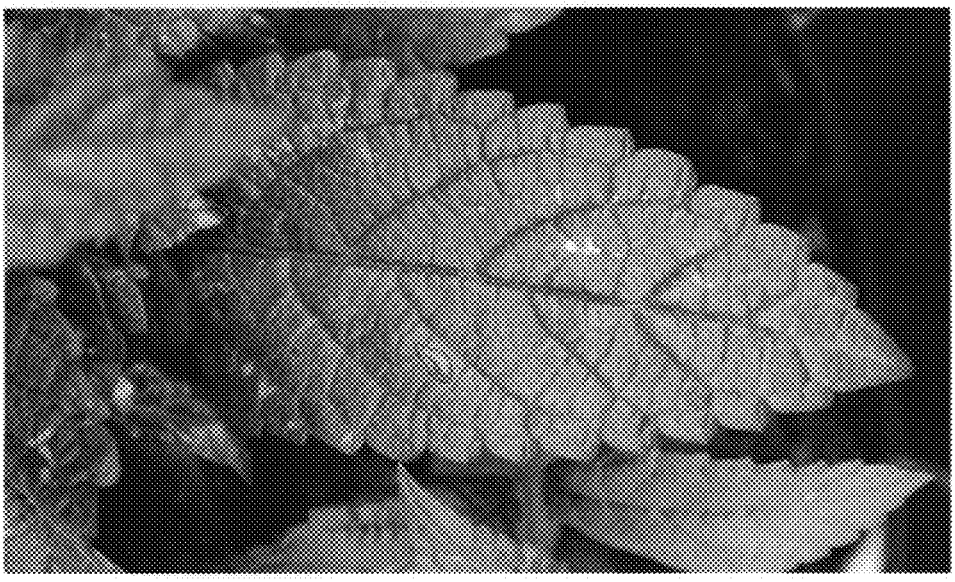

The photograph in FIG. 3 provides a close-up view of the foliage of 'Bokratune'.

The colors in the photographs may differ slightly from the color values cited in the detailed botanical description, which accurately describe the colors of the new *Nepeta.*

DETAILED BOTANICAL DESCRIPTION

The following is a detailed description of the new cultivar of plants 12 months in age as grown outdoors in 17-cm containers in Boskoop, The Netherlands. The plants were grown under average day temperatures of 15° C. to 30° C. and average night temperatures of 10° C. to 20° C. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period.*—6 weeks from midsummer into fall in the Netherlands with re-blooming occurring after deadheading in about 4 weeks.

*Plant type.*—Herbaceous perennial.

*Plant habit.*—Upright and compact.

*Plant size.*—Average of 35 cm in height and 30 cm in diameter.

*Cold hardiness.*—At least in U.S.D.A. Zones 4 to 10.

*Diseases and pests.*—No susceptibility or resistance to diseases or pests has been observed.

*Root description.*—Fibrous and fine.

*Root development.*—About 8 weeks to initiate roots and 9 months to produce a flowering plant.

*Propagation.*—Stem cuttings.

*Growth rate.*—Low to moderately vigorous.

Stem description:

*Shape.*—Quadrangular.

*Stem color.*—Young stem; 145A, mature stems; 146B to 146C.

*Stem size.*—Average of 12.9 cm in length, 2.5 mm in diameter.

*Stem surface.*—Slightly glossy and densely covered with very short soft hairs, average of 0.5 mm in length and too small to measure color.

*Stem aspect.*—Held at varying angles between 35° to 25°.

*Internode length.*—Average of 2.6 cm.

*Branching.*—Average of 6 primary branches and 4 lateral branches.

*Stem strength.*—Strong.

Foliage description:

*Leaf shape.*—Ovate.

*Leaf division.*—Simple.

*Leaf base.*—Truncate.

*Leaf apex.*—Acute.

*Leaf venation.*—Pinnate, upper and lower surface color; 144A.

*Leaf margins.*—Serrate.

*Leaf arrangement.*—Opposite.

*Leaf attachment.*—Petiolate.

*Leaf surface.*—Upper surface; moderately rugose and slightly glossy, lower surface; slightly rugose and matte, both surfaces; moderately pubescent with very short hairs; an average of 0.3 mm in length and too small to measure color.

*Leaf size.*—Up to 6.7 cm in length and 3.3 cm in width.

*Leaf color.*—Young upper surface; 143A, young lower surface; 143B to 143C, mature upper surface; NN137A to NN137B, mature lower surface; 147B.

*Leaf color.*—Typical *Nepeta kubanica* scent when touched; moderately strong, pleasant and slightly minty.

*Petioles.*—An average of 7 mm in length and 2 mm in diameter, upper surface color 144A, lower surface color 144B, strong, upper surface matte, lower surface moderately glossy, both surfaces moderately covered with very short pubescent hairs; an average of 0.3 mm in length and too small to measure color.

Inflorescence description:

*Inflorescence type.*—Terminal raceme of labiate flowers.

*Lastingness of inflorescence.*—Individual flowers average of 5 days, self cleaning.

*Inflorescence size.*—An average of 8.3 cm in height and 4.5 cm in diameter.

*Flower type.*—Labiate.

*Flower aspect.*—Outward.

*Flower number.*—Average of 144.

*Flower fragrance.*—None.

*Flower buds.*—Oblanceolate in shape, 6 mm in length, 3 mm in diameter, matte surface, moderately covered with very short hairs an average of 0.3 mm in length and too small to measure color, color ranging between N186A and N186C, base 144C.

*Flower size.*—Average of 1 cm in height, 5 mm in diameter, 2.2 cm in length, throat diameter is 4 mm, tube length is 1.2 cm, tube diameter 2.5 mm.

*Peduncle.*—An average of 6.2 cm in length and 1.75 mm in diameter, 146B to 146C in color, held straight on top of lateral branch, strong in strength, surface is matte and moderately pubescent, short hairs an average of 0.3 mm in length and too small to measure color.

*Pedicels.*—Average of 4 mm in length, 1 mm in diameter, 144A in color, held at an average angle of 40° (0°=straight upright), moderately strong in strength, surface is slightly glossy and moderately pubescent with short hairs an average of 0.2 mm in length and too small to measure color.

*Calyx.*—Rotate and tubular in shape, average of 1 cm in length and 4.5 mm in diameter.

*Sepals.*—5, rotate, base is fused 70%, lanceolate in shape, entire margin, 30% of apex is free and narrow acute, campanulate arrangement, 1 cm in length, 1.5 mm in width, entire margins, upper surface is glabrous and smooth, lower surface is slightly glossy and matte, both surfaces are moderately pubescent with very short hairs an average of 0.2 mm in length and too small to measure color, upper and lower surface when opening and fully open between N186A and N186C, base 144C.

*Petals.*—5, fused at base 55%, labiate, upper lip; oblanceolate in shape, margin entire, apex obtuse, 1.6 cm in length and 3 mm in width, based fused, upper and lower surface smooth, matte, glabrous, moderately pubescent with very short hairs an average of 0.2 mm in length and too small to measure color, lower lip; spathulate to oblanceolate in shape, margin entire, apex of lower cleft into two lobes, tip of lobes obtuse, 1.8 cm in length and 5 mm in width, base fused, upper and lower surface smooth, glabrous, matte, moderately pubescent with very short hairs on the lower surface an average of 0.2 mm in length, upper surface 0.3 mm in length and too small to measure color, throat texture inner and outer surface smooth and glabrous, tube texture inner surface smooth and glabrous, tube texture outer surface moderately pubescent with very short hairs an average of 0.2 mm in length and too small to measure color, color; upper surface when opening and fully open N88A, central and free portion a blend of N80B, N81B to N81C, lower surface when opening and fully opening N88A.

Reproductive organs:

*Gynoecium.*—Pistil; 1, 2.3 cm in length, style; 2.1 cm in length, N80B to N80C in color, stigma; cleft (2 parted), 1.5 mm in diameter and N81A in color, ovary; N144A in color.

*Androecium.*—Stamens; 4, filaments; 90B to 90C in color, 7 mm in length, anthers; dorsifixed, narrow elliptic in shape, 1 mm in length, 0.5 mm in width, N92C in color, pollen; moderate in quantity and N155A in color.

*Fruit and seed.*—None been observed to date.

It is claimed:

1. A new and distinct cultivar of *Nepeta* plant named 'Bokratune' as herein illustrated and described.

* * * * *